United States Patent [19]

Kurazumi et al.

[11] Patent Number: 5,405,840
[45] Date of Patent: Apr. 11, 1995

[54] PRANOPROFEN-CONTAINING, SUSPENDING MEDICINAL COMPOSITION

[75] Inventors: Toshiaki Kurazumi, Narita; Katsumi Imamori; Akira Iwasa, both of Yotsukaido, all of Japan

[73] Assignee: SS Pharmaceutical Co., Ltd., Tokyo, Japan

[21] Appl. No.: 27,095

[22] Filed: Mar. 5, 1993

[30] Foreign Application Priority Data

Mar. 10, 1992 [JP] Japan .................. 4-051641

[51] Int. Cl.$^6$ .................. A61K 9/10; A61K 9/66; A61K 31/715
[52] U.S. Cl. .................. 514/57; 514/772; 514/777; 514/781; 514/937; 514/969; 514/970
[58] Field of Search .................. 514/57, 772, 777, 781, 514/969, 970, 937

[56] References Cited

U.S. PATENT DOCUMENTS

| 4,474,766 | 10/1984 | Goldenberg et al. | 424/177 |
| 5,182,112 | 1/1993 | Kurazumi et al. | 424/439 |
| 5,225,206 | 7/1993 | Fushimi et al. | 424/490 |

FOREIGN PATENT DOCUMENTS 0468232  1/1992  European Pat. Off.
2224129  10/1974  France.

OTHER PUBLICATIONS

Sprowl's American Pharmacy, pp. 163–167, "Lyophilic Colloidal Systems".
Patent Abstracts of Japan, vol. 4, No. 69 (C–11) (551), May 22, 1980, JP-A-55 035 047, Mar. 11, 1980.

Primary Examiner—Ronald W. Griffin
Attorney, Agent, or Firm—Oblon, Spivak, McClelland, Maier & Neustadt

[57] ABSTRACT

A pranoprofen-containing, suspending medicinal composition is formed of the following three ingredients (a) to (c):
(a) pranoprofen;
(b) a suspending agent comprising microcrystalline cellulose-sodium carboxymethylcellulose, sodium carboxymethylcellulose and hydroxypropyl methylcellulose; and
(c) a saccharide solution.

4 Claims, No Drawings

PRANOPROFEN-CONTAINING, SUSPENDING MEDICINAL COMPOSITION

BACKGROUND OF THE INVENTION a. Field of the Invention

The present invention relates to pranoprofen-containing, suspending medicinal compositions, and more specifically to pranoprofen-containing, suspending medicinal compositions, such as syrups, which feature good long-term stability of pranoprofen, remain in a well-dispersed state with good fluidity over a prolonged period of time, and are palatable.

b. Description of the Related Art

Pranoprofen is a non-steroidal anti-inflammatory agent having excellent anti-inflammatory effects and analgesic effects and is considered to have a small incidence rate of side effects. It has therefore found increasing utility, especially in the field of pediatrics. As dosable preparation forms for use in the field of pediatrics, syrups are desired.

With a view toward preparing syrups of pranoprofen, the present inventors have therefore proceeded with a variety of research. As a result, it has been found that pranoprofen exhibits poor stability when prepared into a dissolving syrup and a suspending syrup is hence preferred for pranoprofen from the standpoint of stability.

Suspending medicinal compositions, led by suspending syrups, are however required to contain an effective ingredient evenly in the compositions without settling and further to readily flow out of containers as needed. They are accordingly required to remain in a well-dispersed state with good fluidity over a prolonged period of time.

To fulfill such requirements, the following methods are generally used: (1) to reduce the size of suspended particles, (2) to minimize the difference in density between the suspended particles and a dispersion medium, and (3) to increase the viscosity of the dispersion medium. Although some improvements can be observed according to the method (1) or (2), the method (3) is accompanied by the drawback that higher viscosity naturally leads to poor fluidity thereby making it difficult to dispense the suspending medicinal composition into smaller containers and also to administer the composition. It has therefore been difficult to prepare a pranoprofen-containing suspending medicinal composition which remains in a well-dispersed state with good fluidity over a prolonged period of time.

SUMMARY OF THE INVENTION

With the foregoing in view, the present inventors have carried out an extensive investigation. As a result, it has now been found that combined incorporation of microcrystalline cellulose-sodium carboxymethylcellulose (trade name: "AVICEL RC"), sodium carboxymethylcellulose and hydroxypropyl methylcellulose as a suspending agent can provide a pranoprofen-containing, suspending medicinal composition which, even when stored over a long period of time, remains in a well-dispersed state without settling of particles while retaining good fluidity, leading to the completion of the present invention.

In one aspect of this invention, there is thus provided a pranoprofen-containing, suspending medicinal composition which comprises the following three ingredients (a) to (c):

(a) pranoprofen;
(b) a suspending agent comprising microcrystalline cellulose-sodium carboxymethylcellulose, sodium carboxymethylcellulose and hydroxypropyl methylcellulose; and
(c) a saccharide solution.

The pranoprofen-containing, suspending medicinal composition according to the present invention features good long-term stability of pranoprofen and remains free from settling of particles over a prolonged period of time while maintaining good fluidity. Accordingly, the pranoprofen-containing, suspending medicinal composition has such advantages as easy handling and high palatability.

DETAILED DESCRIPTION OF THE INVENTION AND PREFERRED EMBODIMENTS

In the present invention, pranoprofen as the ingredient (a) is in the form of water-insoluble crystals. Upon mixing, it is therefore necessary to grind pranoprofen so that its particle size is reduced.

In general, it is preferred to grind pranoprofen to a particle size of 1–15 $\mu$m or so, followed by its preparation into a suspending medicinal composition according to the present invention. Although no particular limitation is imposed on the content of pranoprofen, it is preferable to control its content in a range of 0.1–10 wt. % based on the whole composition.

For the suspending agent as the ingredient (b), on the other hand, it is essential that the three compounds, namely, microcrystalline cellulose-sodium carboxymethylcellulose, sodium carboxymethylcellulose and hydroxypropyl methylcellulose are added together. No good suspending agent can be obtained even if only one of the three components is omitted. It is preferred to proportion them in such a way that, when the resulting suspending agent is incorporated in the composition, the viscosity finally falls within a range of 100–1,000 cps at 20° C. This viscosity range can be obtained, for example, by adding microcrystalline cellulose-sodium carboxymethylcellulose ("AVICEL RC") in an amount of 0.5–1.5 wt. % (hereinafter simply referred to as "%"), sodium carboxymethylcellulose in an amount of 0.1–0.5% and hydroxypropylmethylcellulose in an amount of 0.1–0.5%, all based on the composition.

As the saccharide solution as the ingredient (C), any saccharide solution usable as a syrup base can be used in general. Examples of the saccharide solution includes solutions of saccharides such as sucrose, glucose, fructose, liquid sucrose and sorbitol. The preferred content of the saccharide solution may range from 20% to 70% or so in terms of the saccharide based on the composition.

The suspending medicinal composition according to the present invention can be prepared by uniformly mixing the above-described ingredients in a manner known per se in the art.

For insolubilizing pranoprofen to provide a suspending system, the pH of the composition preferably ranges from 3 to 6.

The suspending medicinal composition according to the present invention can contain, in addition to the essential ingredients described above, one or more of known antiseptics, dispersants, pH regulators and the like to an extent not impairing the advantages of the present invention. Illustrative usable antiseptics include sodium benzoate and butyl paraoxybenzoate. Exemplary usable dispersants include polyoxyethylene hydrogenated castor oil, polysorbate 80, and sugar fatty acid esters. Illustrative usable pH regulators include hydrochloric acid, citric acid and sodium hydroxide.

The present invention will next be described by the following examples and tests.

EXAMPLES 1-7 AND COMPARATIVE EXAMPLES 1-7

Syrups whose formulations are shown in Tables 1 and 2, respectively, were prepared by the following preparation procedure and after being left over standstill, their viscosities were measured. The results are also presented in the same tables.

Preparation Procedure of Suspending Syrups of Examples 1-7 and Syrups of Comparative Examples 2-7

In each of the examples and comparative examples, sodium benzoate and sucrose in the amounts shown in Table 1 were dissolved in purified warm water in an amount as needed, followed by the addition of "AVICEL RC", sodium carboxymethylcellulose and/or hydroxypropyl methylcellulose in the amounts as shown in Table 1 or 2. The resulting mixture was agitated and dispersed in a homomixer. A dispersion of 1.5 g of pranoprofen in an aqueous solution, in which 0.1 g of a sucrose-fatty acid ester was contained, was then added, followed by stirring. The suspension so obtained was adjusted to pH 5.0 with hydrochloric acid or sodium hydroxide, followed by the addition of purified water in an amount as needed to give a total volume of 100 ml.

Preparation Procedure of Syrup of Comparative Example 1

Sodium benzoate (0.07 g) was dissolved in purified warm water in an amount as desired, followed by the addition of 1.5 g of pranoprofen. Sodium hydroxide was added further and pranoprofen was then dissolved under stirring. Sucrose (50 g) was then added, followed by the adjustment to pH 7.0 with hydrochloric acid or sodium hydroxide. Purified water was then added in an amount as needed to give a total volume of 100 ml.

TABLE 1

| Ingredient | Example 1 | Example 2 | Example 3 | Example 4 | Example 5 | Example 6 | Example 7 |
| --- | --- | --- | --- | --- | --- | --- | --- |
| Pranoprofen | 1.5 g | 1.5 g | 1.5 g | 1.5 g | 1.5 g | 1.5 g | 1.5 g |
| "AVICEL RC" | 0.5 | 1.0 | 1.0 | 1.0 | 1.5 | 1.5 | 1.5 |
| Sodium carboxymethylcellulose | 0.5 | 0.2 | 0.2 | 0.4 | 0.4 | 0.1 | 0.1 |
| Hydroxypropyl methylcellulose | 0.5 | 0.2 | 0.4 | 0.2 | 0.4 | 0.1 | 0.4 |
| Sucrose | 50.0 | 50.0 | 50.0 | 50.0 | 50.0 | 50.0 | 50.0 |
| Sodium benzoate | 0.07 | 0.07 | 0.07 | 0.07 | 0.07 | 0.07 | 0.07 |
| Sucrose fatty acid ester | 0.1 | 0.1 | 0.1 | 0.1 | 0.1 | 0.1 | 0.1 |
| Hydrochloric acid or sodium hydroxide | as needed | as needed | as needed | as needed | as needed | as needed | as needed |
| Purified water | to 100 ml | to 100 ml | to 100 ml | to 100 ml | to 100 ml | to 100 ml | to 100 ml |
| Viscosity at 20° C. when left over standstill, cps | 220 | 360 | 370 | 510 | 540 | 790 | 850 |

TABLE 2

| Ingredient | Comparative Example 1 | Comparative Example 2 | Comparative Example 3 | Comparative Example 4 | Comparative Example 5 | Comparative Example 6 | Comparative Example 7 |
| --- | --- | --- | --- | --- | --- | --- | --- |
| Pranoprofen | 1.5 g | 1.5 g | 1.5 g | 1.5 g | 1.5 g | 1.5 g | 1.5 g |
| "AVICEL RC" | — | 0.5 | 0.5 | 1.0 | 1.0 | 1.5 | 2.0 |
| Sodium carboxymethylcellulose | — | 0.5 | — | 0.4 | — | 0.1 | — |
| Hydroxypropyl methylcellulose | — | — | 0.5 | — | 0.4 | — | — |
| Sucrose | 50.0 | 50.0 | 50.0 | 50.0 | 50.0 | 50.0 | 50.0 |
| Sodium benzoate | 0.07 | 0.07 | 0.07 | 0.07 | 0.07 | 0.07 | 0.07 |
| Sucrose fatty acid ester | 0.1 | 0.1 | 0.1 | 0.1 | 0.1 | 0.1 | 0.1 |
| Hydrochloric acid or Sodium hydroxide | as needed | as needed | as needed | as needed | as needed | as needed | as needed |
| Purified water | to 100 ml | to 100 ml | to 100 ml | to 100 ml | to 100 ml | to 100 ml | to 100 ml |
| Viscosity at 20° C. when left over standstill, cps | — | 200 | 120 | 560 | 320 | 1200 | 1550 |

Test 1

Samples of Example 1 and Comparative Example 1 were placed in amber-colored glass bottles, respectively. After they were either exposed to ultraviolet rays of 1,000 lux for one day or stored at 70° C. for 1 week, a predetermined constant amount of each sample was sampled and then diluted to about 10 μg/ml with acetonitrile. The content of pranoprofen was measured by high-performance liquid chromatography (HPLC) under the below-described conditions to determine the stability of pranoprofen.

| HPLC conditions | |
| --- | --- |
| Column size: | 4.6 mm (diameter) 250 mm (length). |
| Column packing material: | ODS (octadecyl sila- |

TABLE 4

| Property | Example 1 | Example 2 | Example 3 | Example 4 | Example 5 | Example 6 | Example 7 |
|---|---|---|---|---|---|---|---|
| Dispersion properties | A | A | A | A | A | A | A |
| Fluidity | A | A | A | A | A | A | A |
| Viscosity at 20° C. when left over standstill, cps | 250 | 430 | 430 | 550 | 570 | 880 | 880 |

Dispersion properties: A: No settling.
Fluidity: A: Fluid.

TABLE 5

| Property | Comparative Example 2 | Comparative Example 3 | Comparative Example 4 | Comparative Example 5 | Comparative Example 6 | Comparative Example 7 |
|---|---|---|---|---|---|---|
| Dispersion properties | B | B | B | B | A | A |
| Fluidity | A | A | A | A | B | B |
| Viscosity at 20° C. when left over standstill, cps | 220 | 150 | 650 | 350 | 1350 | 1700 |

Dispersion properties: A: No settling. B: Settled.
Fluidity: A: Fluid. B: No fluidity.

| HPLC conditions | |
|---|---|
| Mobile phase: | nized silica gel). 1:1 mixed solvent of acetonitrile and 0.6% aqueous solution of tartaric acid. |
| Measuring wavelength: | 245 nm. |
| Flow rate: | 1 ml/min. |

TABLE 3

| | Example 1 | Comp. Ex. 1 |
|---|---|---|
| UV exposure (1 day) | 100.5% | 87.0% |
| 70° C. (1 week) | 99.4% | 93.5% |

As is clearly envisaged from Table 3, the suspending system of Example 1 was more stable to light and heat than the dissolving system of Comparative Example 1.

Test 2

Samples of Examples 1–7 and Comparative Examples 2–7 were placed in amber-colored glass bottles, respectively, and then stored at 40° C. for 1 month. They were compared in the state of dispersion and fluidity. The results are summarized in Tables 4 and 5.

As is shown in Tables 4 and 5, the compositions of Examples 1–7, different from the compositions of the comparative examples, remained free from settling and retained good fluidity during the one-month test period.

We claim:
1. A pranoprofen-containing, suspending medicinal composition comprising the following three ingredients (a) to (c):
   (a) pranoprofen in an amount sufficient for administering therapeutic dosages and having a particle size of about 1–15 μm;
   (b) a suspending agent comprising 0.5–1.5% by weight of microcrystalline cellulose-sodium carboxymethylcellulose, 0.1–0.5% by weight of sodium carboxymethylcellulose and 0.1–0.5% by weight of hydroxypropyl methylcellulose; and
   (c) a saccharide solution.
2. A composition of claim 1, which has a pH of 3–6.
3. A composition of claim 1, which has a viscosity of 100–1,000 cps at 20° C.
4. A composition of claim 3, which has a pH of 3–6.

* * * * *